United States Patent
Prasad (10) Patent No.: US 11,826,394 B2
(45) Date of Patent: *Nov. 28, 2023

(54) METHOD OF USING A ROSEMARY EXTRACT COMPOSITION FOR PROMOTING A HEALTHY BODY WEIGHT

(71) Applicant: Kodimule Shyam Prasad, Bangalore (IN)

(72) Inventor: Kodimule Shyam Prasad, Bangalore (IN)

(73) Assignee: Vidya Herbs, Inc., Fullerton, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 17/336,816

(22) Filed: Jun. 2, 2021

(65) Prior Publication Data

US 2021/0361732 A1 Nov. 25, 2021

Related U.S. Application Data

(63) Continuation of application No. 16/558,246, filed on Sep. 2, 2019, now Pat. No. 11,045,514.

(60) Provisional application No. 62/726,881, filed on Sep. 4, 2018.

(51) Int. Cl.

| | | |
|---|---|---|
| *A61K 36/00* | (2006.01) | |
| *A61K 36/53* | (2006.01) | |
| *A61K 31/19* | (2006.01) | |
| *A61K 31/045* | (2006.01) | |
| *A61K 9/68* | (2006.01) | |
| *A61P 3/04* | (2006.01) | |
| *A61K 9/20* | (2006.01) | |
| *A61K 9/48* | (2006.01) | |
| *A23L 33/00* | (2016.01) | |
| *A23L 33/105* | (2016.01) | |
| *A61K 9/00* | (2006.01) | |

(52) U.S. Cl.
CPC ............ *A61K 36/53* (2013.01); *A23L 33/105* (2016.08); *A23L 33/30* (2016.08); *A61K 9/006* (2013.01); *A61K 9/0058* (2013.01); *A61K 9/20* (2013.01); *A61K 9/4808* (2013.01); *A61K 31/045* (2013.01); *A61K 31/19* (2013.01); *A61P 3/04* (2018.01)

(58) Field of Classification Search
CPC ........................................................ A61P 3/04
See application file for complete search history.

(56) References Cited

U.S. PATENT DOCUMENTS

| | | | |
|---|---|---|---|
| 11,045,514 B2 * | 6/2021 | Prasad | ................... A61K 9/006 |
| 2011/0091580 A1 | 4/2011 | He | |
| 2018/0099019 A1 * | 4/2018 | Brownell | ............... A61K 31/12 |

FOREIGN PATENT DOCUMENTS

CN 101422465 A1 5/2009

OTHER PUBLICATIONS

Romo-Vaquero M. et al. A Rosemary Extract Rich in Carnosic Acid Selectively Modulates Caecum Microbiota . . . PLOS One 9(4) 1-11, Apr. 2014. (Year: 2014).*
Seo et al., Ursolic Acid in Heaht and Disease, Korean J of Physiology Pharmacology 22(3)235-248 May 2018.
Vaquero et al., Inhibition of Gastric Lipase as a Mechanism for Body Weight and Plasma Lipids Reduction in Zucker Rats, Plos One 7(6)e39773 Jun. 2012.
Singletary, Rosemary: An Overview of Potential Health Benefits, Nutrition Today 51(2)102-112 Mar. 2016.
Sesatty et al., Investigation of Ursolic Acid Supplement Purity, FASEB J 30 (Suppl 1) 1176.12 2016.

* cited by examiner

*Primary Examiner* — Qiuwen Mi (74) *Attorney, Agent, or Firm* — TMB Law; Timothy M. Brown (57) ABSTRACT

A method of modulating body weight using a composition of rosemary extract having a pre-determined amount of ursolic acid.

18 Claims, 5 Drawing Sheets

METHOD OF USING A ROSEMARY EXTRACT COMPOSITION FOR PROMOTING A HEALTHY BODY WEIGHT

CROSS-REFERENCE TO RELATED APPLICATIONS

This application is a continuation of U.S. application Ser. No. 16/558,246 filed Sep. 2, 2019 which claims the benefit of U.S. Provisional Application No. 62/726,881 filed Sep. 4, 2018. The entire contents of these applications are incorporated herein by reference for all purposes.

FIELD OF THE INVENTION

The invention generally relates to treatments for health and weight management. More particularly, the invention relates to a composition derived from rosemary and a method of its use in weight management.

BACKGROUND

Rosemary is a spice and medicinal herb belonging to the family Lamiaceae. Rosemary is indigenous to the Mediterranean region and South America and has been widely used around the world for its culinary and medicinal uses. Rosemary extract and its polyphenolic constituents have been reported to have a number of beneficial properties, including antioxidant, anti-inflammatory, and anticancer effects. Rosemary contains a plethora of bioactive constituents. The main polyphenols found in rosemary extract include the diterpenes carnosic acid and rosmarinic acid. The present invention provides a composition derived from rosemary and its method of use for managing body weight.

SUMMARY OF THE INVENTION

The inventor discovered a composition of rosemary extract and ursolic acid which provides unexpected efficacy in the management of body weight. Thus, it is an object of the invention to provide a method of modulating body weight wherein the method comprises administering to a patient in need thereof a composition comprising rosemary extract, wherein the extract comprises ursolic acid. In at least one embodiment, the extract comprises about 50% ursolic acid.

DEFINITIONS

As used herein, the term "about" means the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% of the referenced quantity, level, value, number, frequency, percentage, dimension, size, amount, weight or length.

Throughout this specification, unless the context requires otherwise, the words "comprise," "comprises," and "comprising" will be understood to refer to the inclusion of a stated step or element, or group of steps or elements, but not the exclusion of any other step or element or group of steps or elements.

As used herein, the phrases "effective amount," "effective dose," and "therapeutically effective amount," refer to that amount of a therapeutic agent sufficient to ameliorate a disorder, disease or condition, or the symptoms of a disorder, disease or condition. For example, for the given parameter, a therapeutically effective amount will show an increase or decrease of therapeutic effect that is at least 5%, at least 10%, at least 15%, at least 20%, at least 25%, at least 40%, at least 50%, at least 60%, at least 75%, at least 80%, at least 90%, or at least 100%. Therapeutic efficacy can also be expressed as a "-fold" increase or decrease. For example, a therapeutically effective amount can have at least a 1.2-fold, 1.5-fold, 2-fold, 5-fold, or more effect over a control.

As used herein, the term "increase" refers to any measurable increase in a parameter relative to control conditions.

As used herein, the term "reduce" refers to any measurable decrease in a parameter relative to control conditions.

As used herein, the terms "subject," "patient," "individual" and like terms are used interchangeably and refer to, except where indicated, mammals such as humans and non-human primates, as well as livestock and companion and laboratory research animals.

DETAILED DESCRIPTION

The invention generally relates to compositions and methods for their use in modulating body weight. More particularly, the invention provides a composition comprising rosemary extract and ursolic acid and a method of making and using the composition in weight management.

The inventor surprisingly discovered a composition of rosemary extract with ursolic acid that can be highly effective in managing a patient's body weight. As exemplified by the present disclosure, the composition has demonstrated effects on many aspects of the physiological regulation of body weight. In particular, the inventor has shown that the composition can inhibit pancreatic lipase and impact adipocyte development. The inventor further demonstrated that the composition can impact the expression and activity of proteins involved in weight metabolism, including the transcription factors PPARγ and C/EBPα which are known adipogenesis regulators.

In some aspects, the invention provides a composition. The composition can comprise rosemary extract. The composition can comprise rosemary extract, wherein the extract comprises ursolic acid. The extract can comprise ursolic acid in a specific amount. The extract can comprise between about 5% w/w and about 70% w/w ursolic acid. The extract can comprise between about 5% and about 10% ursolic acid. The extract can comprise between about 10% and about 15% ursolic acid. The extract can comprise between about 15% and about 20% ursolic acid. The extract can comprise between about 20% and about 25% ursolic acid. The extract can comprise between about 25% and about 30% ursolic acid. The extract can comprise between about 30% and about 35% ursolic acid. The extract can comprise between about 35% and about 40% ursolic acid. The extract can comprise between about 40% and about 45% ursolic acid. The extract can comprise between about 45% and about 50% ursolic acid. The extract can comprise between about 50% and about 55% ursolic acid. The extract can comprise between about 55% and about 60% ursolic acid. The extract can comprise between about 60% and about 65% ursolic acid. The extract can comprise between about 65% and about 70% ursolic acid. The extract can comprise up to about 5%, up to about 10%, up to about 15%, up to about 20%, up to about 30%, up to about 35%, up to about 40%, up to about 45%, up to about 50%, up to about 55%, up to about 60%, up to about 65%, or up to about 70% w/w ursolic acid. In one non-limiting embodiment, the composition comprises rosemary extract, wherein the extract comprises about 50% w/w ursolic acid. It will be understood by one skilled in the art that, unless otherwise indicated by context, all percentages used to refer to the amount of a component disclosed herein shall refer to the weight to weight percentage of that component relative to the sum total of the components that are present in a given substance. For example, a composition comprising rosemary extract, wherein the extract comprises 50% w/w ursolic acid means that 50% of the total weight of the extract is formed from ursolic acid.

In some aspects, the composition of the invention comprises at least one excipient. The composition can comprise at least one carrier. The composition can comprise at least one excipient and at least one carrier. The excipient and/or carrier can be selected on the basis of compatibility with rosemary extract and the properties of the desired dosage form. Suitable excipients include, but are not limited to, binders, fillers, bulking agents, flow aids/glidents, disintegrants, lubricants, stabilizers, surfactants, and the like. The excipient can be selected from the group consisting of binders, fillers, bulking agents, flow aids/glidents, disintegrants, lubricants, stabilizers, surfactants, and combinations thereof. Suitable excipients and carriers for use with the composition include, but are not limited to, those disclosed in: Remington: The Science and Practice of Pharmacy, 19th Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999). The entire contents of these publications are incorporated herein by reference for all purposes.

In some aspects of the invention, the composition employs controlled, sustained, or extended release formulations known collectively as "modified release" formulations. The composition can be administered by modified release systems or by delivery devices known to those skilled in the art. Suitable examples of such systems and delivery devices include, but are not limited to, those described in the following U.S. Patents, the entire disclosures of which are incorporated herein by reference for all purposes: U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Dosage forms for the composition can be used to provide modified release of one or more active ingredients using, for example, hydropropylmethyl cellulose, other polymer matrices, gels, permeable membranes, osmotic systems, multilayer coatings, microparticles, liposomes, microspheres, or combinations thereof.

At least one aspect of the invention concerns the dosage form of the composition. The composition can be in the form of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, injection, or combinations thereof. The composition can be formulated for oral administration. The composition can be combined with vitamins, minerals, amino acids, proteins, extracts, carbohydrates, lipids, fatty acids, caffeine, flavorings, sweeteners, preservatives, or combinations thereof.

In some aspects of the invention, the composition is combined with a food, snack, nutritional supplement, dietary supplement, food supplement, or beverage. The food, snack, nutritional supplement, dietary supplement, food supplement, or beverage can have reduced calorie content. For example, the composition can be provided as a means for managing body weight wherein the composition is formulated to provide a dietetic food, a dietetic snack, a dietetic nutritional supplement, a dietetic dietary supplement, a dietetic food supplement, or a dietetic beverage. The composition can be combined with dietetic snacks such as bars, chips, chews, gels, candies, chocolates, cakes, cookies and other pastries, wafers, crackers, ice cream, and the like.

The composition can be provided in bulk quantities for the industrial manufacture of the products and dosage forms described herein. For example, the composition can be provided in bulk quantities as a powder or liquid. Bulk quantities of the composition can be packaged, stored and/or distributed in drums, bags, boxes, and other containers which are configured to prevent or inhibit the oxidation of the active components of the composition, such as, for example, ursolic acid.

In some aspects, the invention provides a method of modulating body weight in a patient. The method can be practiced by administering to the patient the composition of the present invention. In a preferred embodiment, the composition is administered in an effective amount. The composition can be administered to the patient to reduce body weight, or to inhibit or prevent weight gain in the patient. For example, the composition can be administered to maintain a desired body weight in the patient. Administering the composition can reduce body fat in the patient, or inhibit or prevent an increase in body fat in the patient. The patient can be obese, overweight or have a normal body weight. The terms "obese" and "obesity" as used herein refer to a patient having a body mass index of 30 or higher. The term "overweight" as used herein refers to a patient having a body mass index of 25 to 29.9. The term "healthy weight" as used herein refers to a patient having a body mass index of 18.5 to 24.9.

Without being limited to any particular theory or mechanism, administering the composition can impart its effect by, among other means, inhibiting one or more forms of lipase in the patient. Lipases (e.g. triacylglycerol hydrolase E.C. 3.1.1.3) are enzymes that catalyze the hydrolysis of ester bonds of triacylglycerols (fats and oils) to produce free fatty acids such as diacylglycerols, monoglycerols and glycerol. In the small intestine of mammals, the digestion of dietary triacylglycerols (TAG) is essentially due to the action of pancreatic lipase. The end products of TAG digestion are absorbed by the body and are responsible for the development of weight gain and obesity. Therefore, if the hydrolysis of TAG and its movement from the intestinal lumen into the body is stopped or minimized, the prevalence of obesity can be reduced. The composition can inhibit pancreatic lipase, pancreatic lipase related protein 2, hepatic lipase, endothelial lipase, and lipoprotein lipase. In one non-limiting embodiment, administering the composition inhibits pancreatic lipase in the patient.

At least one aspect of the invention concerns the dosage at which the composition is administered to the patient. The composition can be administered at a dose of between about 5 mg/day and about 500 mg/day. The composition can be administered at a dose between about 20 mg/day and about 1 mg/day. The composition can be administered at a dose of about 20 mg/day, about 21 mg/day, about 22 mg/day, about 23 mg/day, about 24 mg/day, about 25 mg/day, about 26 mg/day, about 27 mg/day, about 27 mg/day, about 28 mg/day, about 29 mg/day, about 30 mg/day, about 31 mg/day, about 32 mg/day, about 33 mg/day, about 34 mg/day, about 35 mg/day, about 40 mg/day, about 45 mg/day, about 50 mg/day, about 100 mg/day, about 150 mg/day, about 200 mg/day, about 250 mg/day, about 300 mg/day, about 350 mg/day, about 400 mg/day, about 450 mg/day, or about 500 mg/day, as well as any dosage intervening these specifically disclosed amounts. The composition can be administered at a dosage of between about 400 mg/day and about 500 mg/day, between about 300 mg/day and about 400 mg/day, between about 200 mg/day and about 300 mg/day, between about 100 mg/day and about 200 mg/day, or about 20 mg/day and about 100 mg/day. It is contemplated that the composition can be administered at any dosage that intervenes the dosages called out in this specification.

In some aspects, the dosage of the composition is determined by the body weight of the patient. The composition can be administered between about 5 mg/kg b.w. and about 500 mg/kg b.w. The composition can be administered at about 5 mg/kg b.w., about 10 mg/kg b.w., about 20 mg/kg b.w., about 30 mg/kg b.w., about 40 mg/kg b.w., about 50 mg/kg b.w., about 60 mg/kg b.w., about 70 mg/kg b.w., about 80 mg/kg b.w., about 100 mg/kg b.w., about 120 mg/kg b.w., about 140 mg/kg b.w., about 160 mg/kg b.w., about 180 mg/kg b.w., about 200 mg/kg b.w., about 220 mg/kg b.w., about 240 mg/kg b.w., about 260 mg/kg b.w., about 280 mg/kg b. w., about 300 mg/kg b.w., about 320 mg/kg b. w., about 340 mg/kg b.w., about 360 mg/kg b.w., about 380 mg/kg b.w., about 400 mg/kg b.w., about 420 mg/kg b.w., about 440 mg/kg b.w., about 460 mg/kg b.w., about 480 mg/kg b.w., or about 500 mg/kg b.w. In one non-limiting embodiment of the invention, the composition is administered at about 150 mg/kg b.w. The composition can be administered, one, two, three, four, five or more times. The composition can be administered daily, weekly, monthly, or a combination thereof. The composition can be administered one, two, three, four, five, six or more times per day, per week, or per month. One skilled in the art will appreciate that the administration of the composition can be adjusted according to the patient's response to the treatment.

At least one aspect of the invention concerns the administration route of the composition. The composition can be administered systemically. Suitable administration routes for the composition include, but are not limited to, auricular, buccal, conjunctival, cutaneous, dental, endocervical, endosinusal, endotracheal, enteral, epidural, extra-amniotic, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal dental, intracoronary, intracorporus cavernosum, intradermal, intradiscal, intraductal, intraduodenal, intradural, intraepidermal, intraesophageal, intragastric, intravaginal, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravitreal, laryngeal, nasal, nasogastric, ophthalmic, oral, oropharyngeal, parentera, percutaneous, periarticular, peridural, perineural, periodontal, rectal, inhalation, retrobulbar, soft tissue, subarachnoid, subconjunctival, subcutaneous, sublingual, submucosal, topical, transdermal, transmucosal, transplacental, transtracheal, transtympanic, ureteral, urethral, vaginal, or combinations thereof. In a preferred embodiment, the composition is administered orally.

In at least one aspect, the invention provides a method for making the composition. The composition can be made by providing rosemary extract, and combining the extract with ursolic acid. The rosemary extract can be combined with an amount of ursolic acid to provide a rosemary extract that comprises a desired weight to weight percentage of ursolic acid. The rosemary extract can be contacted with ursolic acid to provide a rosemary extract that comprises a weight to weight ratio of ursolic acid as disclosed herein. For example, the rosemary extract can be contacted with ursolic acid to provide a rosemary extract that comprises 50% w/w ursolic acid. In some aspects, the composition can be made by producing an extract of rosemary, wherein the extracting process produces a rosemary extract that contains a desired amount of ursolic acid. The extracting process can produce a rosemary extract having a ursolic acid content disclosed herein. For example, the extracting process can produce a rosemary extract that comprises about 50% w/w ursolic acid. The rosemary for making the composition can be *Rosmarinus officinalis* L. The extract for making the composition can be derived from the any part of the rosemary plant, including, without limitation, the leaves, twigs, flowering apices, roots, and combinations thereof. The extract can be made using any suitable process, including, without limitation, solvent extraction, extrusion, or a combination thereof. Suitable solvents for obtaining extracts for formulating the composition include, but are not limited to, aqueous solvents, alcohol-based solvents, supercritical fluids, polar organic solvents (such as acetone and methylethyl ketone), or combinations thereof. Non-limiting examples of alcohol-based solvents include, but are not limited to, ethanol, isopropyl alcohol, methanol, and combinations thereof. The supercritical fluid can be, but is not necessarily limited to, carbon dioxide.

The present disclosure is further described in the light of the following examples which are set forth for illustration purposes only and are not to be construed as limiting the scope of the present invention.

EXAMPLES

Materials and Methods

Reagents: Dulbecco's modified Eagle's medium (DMEM) and fetal bovine serum (FBS) were obtained from Gibco BRL (Grand Island, NY, USA). Penicillin-streptomycin, insulin, IBMX, dexamethasone were purchased from Sigma Aldrich (St. Louis, MO, USA). Antibodies against PPAR-γ and C/EBPα were purchased from Santa Cruz Biotechnology (Santa Cruz, CA, USA). Unless otherwise indicated, the following results were achieved with a rosemary extract having 50% w/w ursolic acid.

Pancreatic Lipase Activity

Pancreatic lipase activity of the composition was measured by adopting the method described by Kim, et al. and Zheng, et al.

Cell Culture and Differentiation of 3T3-L1 Preadipocytes

3T3-L1 preadipocyte cells, procured from NCCS Pune, were maintained in DMEM containing 10% FBS. Post-confluent 3T3-L1 preadipocytes (considered as day 0) were incubated in differentiation medium (MDI) containing DMEM, 10% FBS, 0.5 mM IBMX, 1 M dexamethasone, 5μg/mL insulin. After two days, the medium was replaced with DMEM containing 10% FBS and 5μ g/mL insulin, and the medium was changed every two days. The cells were fully differentiated into mature adipocytes on days 6-8.

MTT Assay

Briefly, post confluent 3T3-L1 pre-adipocytes (day 0) were incubated in the presence of various concentrations of the composition (2.5-12.5n/mL) with differentiation medium (MDI) for 48 h. The viability was determined using a 3-(4,5-dimethylthiazol-2-yl)-2,5-diphenyltetrazolium bromide (MTT) assay according to the manufacturer's instructions.

Oil Red O Staining

3T3-L1 cells were washed twice with phosphate-buffered saline (PBS) and fixed with 10% formalin for 30 min. After fixation, the cells were washed with 60% isopropanol for 5 min and then stained with an oil red 0 (ORO) working solution (1.5 mg/mL ORO/60% isopropanol) for 15 min at room temperature. The cells were washed with distilled water and photographed under a light microscope.

Western Blotting

3T3-L1 cells were harvested and lysed in ice-cold lysis buffer containing a protease inhibitor cocktail and 1 mM phenylmethanesulfonyl fluoride for 30 min, followed by centrifugation at 10,000×g for 30 min at 4° C. Proteins (100μg) were subjected to sodium dodecylsulfate polyacrylamide gel electrophoresis and then transferred to PVDF membrane. The membranes were incubated with primary antibodies, followed by incubation with anti-rabbit or anti-mouse secondary antibodies (Santa Cruz Biotechnology) and protein bands were visualized using an enhanced chemiluminescence system (ECL Advance, GE Healthcare).

Statistical Analysis

All the measurements were made in triplicate and all values were represented as mean±standard error. Statistical analysis was performed by one-way analysis of variance ANOVA followed by Dunnett's multiple comparisons to analyze the significance of differences between control and treated groups. All statistical tests were performed at the P<0.05 level of significance.

Results

Effect of Composition on Pancreatic Lipase

Pancreatic lipase is responsible for the hydrolysis of 50-70% of dietary fats to fatty acids (FA) and monoglycerides (MG). Pancreatic lipase inhibition is one means for evaluating an agent's antiobesity effects.

Figure 1:
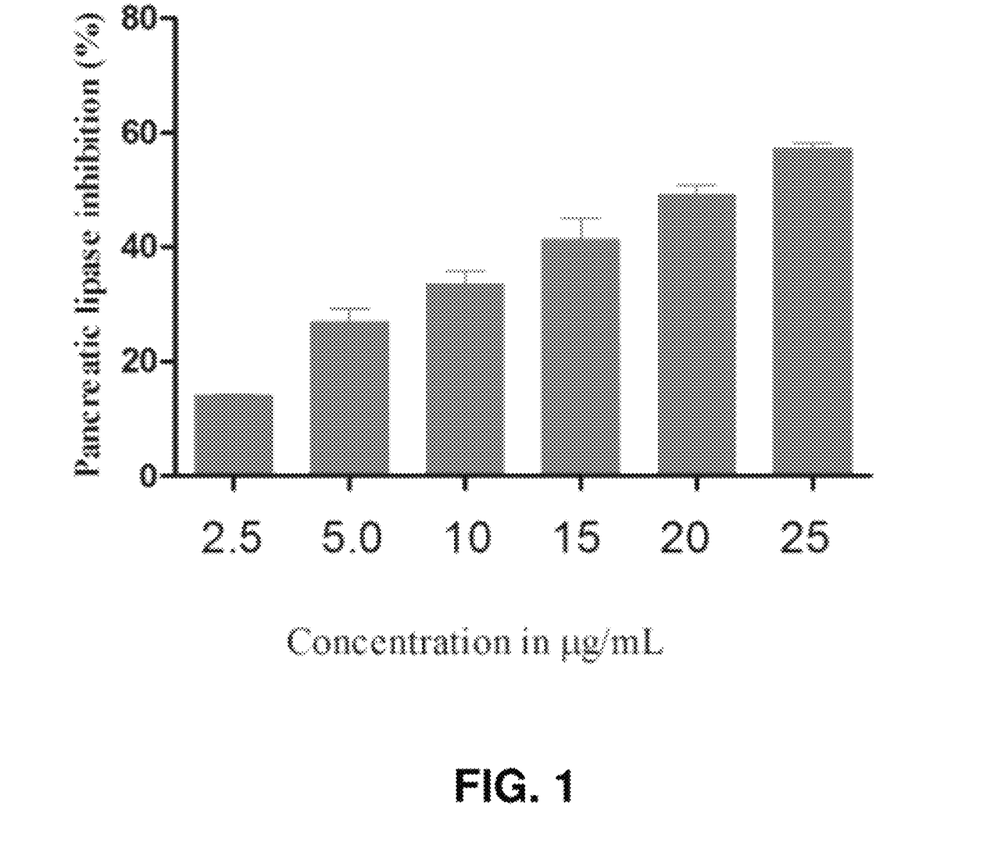
FIG. 1 is a graph showing the inhibitory effect of the composition on pancreatic lipase.

In the current study, the results showed that the composition inhibited pancreatic lipase activity with an IC50 of 20.68μg/mL compared to orlistat having an IC50 of 11.05 μg/mL (FIG. 1).

Effect of Composition on Cell Viability of 3T3L Adipocytes

Figure 2A:
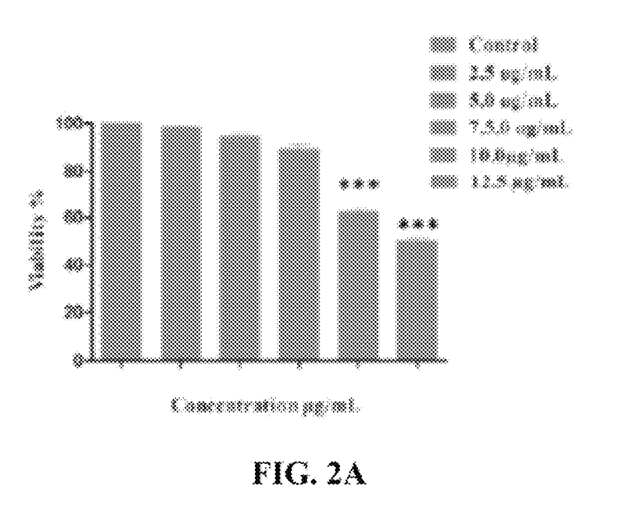
FIG. 2A is a graph showing the effect of the composition on the viability of 3T3-L1 preadipocytes.
Figure 2B:
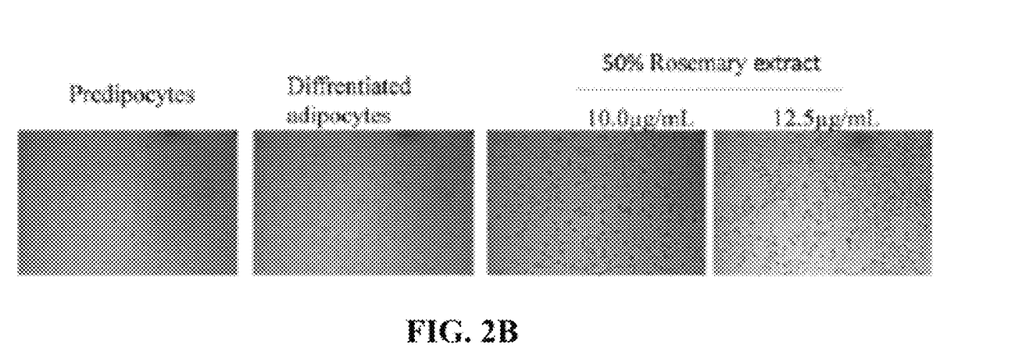
FIG. 2B shows micrographs depicting the effect of the composition on the viability of 3T3-L1 preadipocytes.

The effect of the composition on 3T3-L1 preadipocyte cell viability was evaluated via MTT assay. Post confluent 3T3-L1 preadipocytes were incubated in the presence of various concentrations of the composition with differentiation medium (MDI) for 48 h. The MTT assay showed that the composition did not affect cell viability up to a concentration of 7.5μg/ml, whereas at the concentration of 10μg/ml and 12.5μg/ml, the composition decreased cell viability by approximately 37.52% and 51.44% respectively (FIG. 2A). However, no inhibitory effects on cell viability were observed in cells treated with the composition at a concentration of 7.5μg/ml.

Inhibition of Lipid Accumulation During 3T3-L1 Adipocyte Differentiation

Figure 3A:
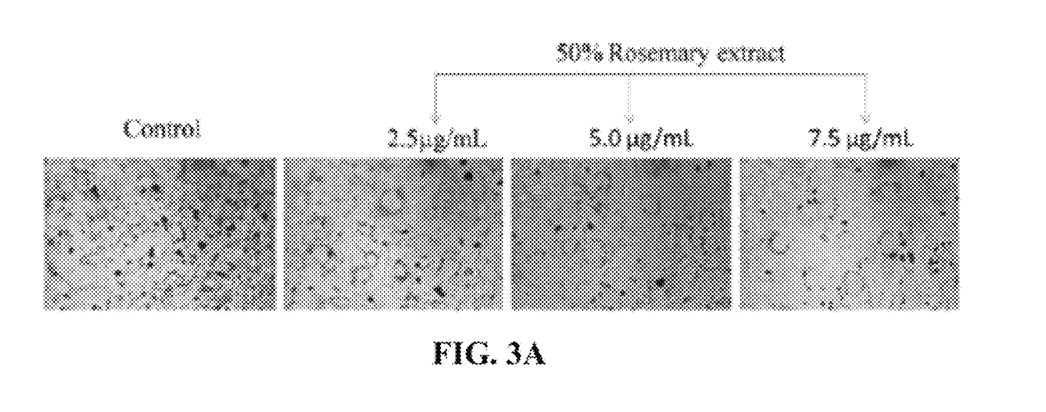
FIG. 3A shows micrographs depicting the effects of the composition on lipid accumulation and differentiation in preadipocytes.
Figure 3B:
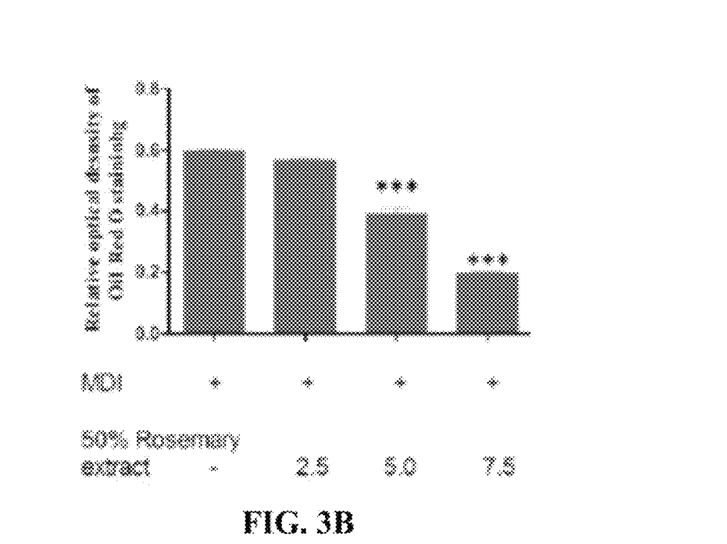
FIG. 3B is a graph that quantifies the effects of the composition on preadipocyte differentiation.

To investigate the effect on lipid accumulation during differentiation, preadipocytes were differentiated into adipocytes in the presence or absence of the composition. Accumulated lipid droplets were stained with fat-specific oil red 0 dye (FIG. 3A). Quantification of ORO staining demonstrated that the composition significantly decreased adipocyte differentiation, resulting in a 66.72% decrease in fat accumulation compared to that of the control group (p<0.001) (FIG. 3B).

The composition inhibits adipogenic differentiation in 3T3-L1 cells. 3T3-L1 preadipocytes were induced to differentiate into adipocytes by MDI cocktail in the presence or absence of the composition (FIG. 3A). After eight days of differentiation, adipocyte differentiation was examined by oil red 0 staining. Intracellular triglyceride accumulation was measured on day 8 of differentiation (FIG. 3B). The data are presented as the mean±SEM of three replicate experiments. *13<0.05, **13<0.001.

Inhibition of Adipogenic Protein Expression

To further evaluate the inhibition of fat accumulation by the composition, protein expression of various adipocyte markers was determined. The transcription factors PPARγ and C/EBPs play a pivotal role in the complex orchestration of transcriptional control during adipogenesis. PPARγ is the master regulator of adipogenesis and is needed to maintain the differentiated state of adipocytes. The expression levels of adipogenesis-related proteins were evaluated using Western blotting.

Figure 4:
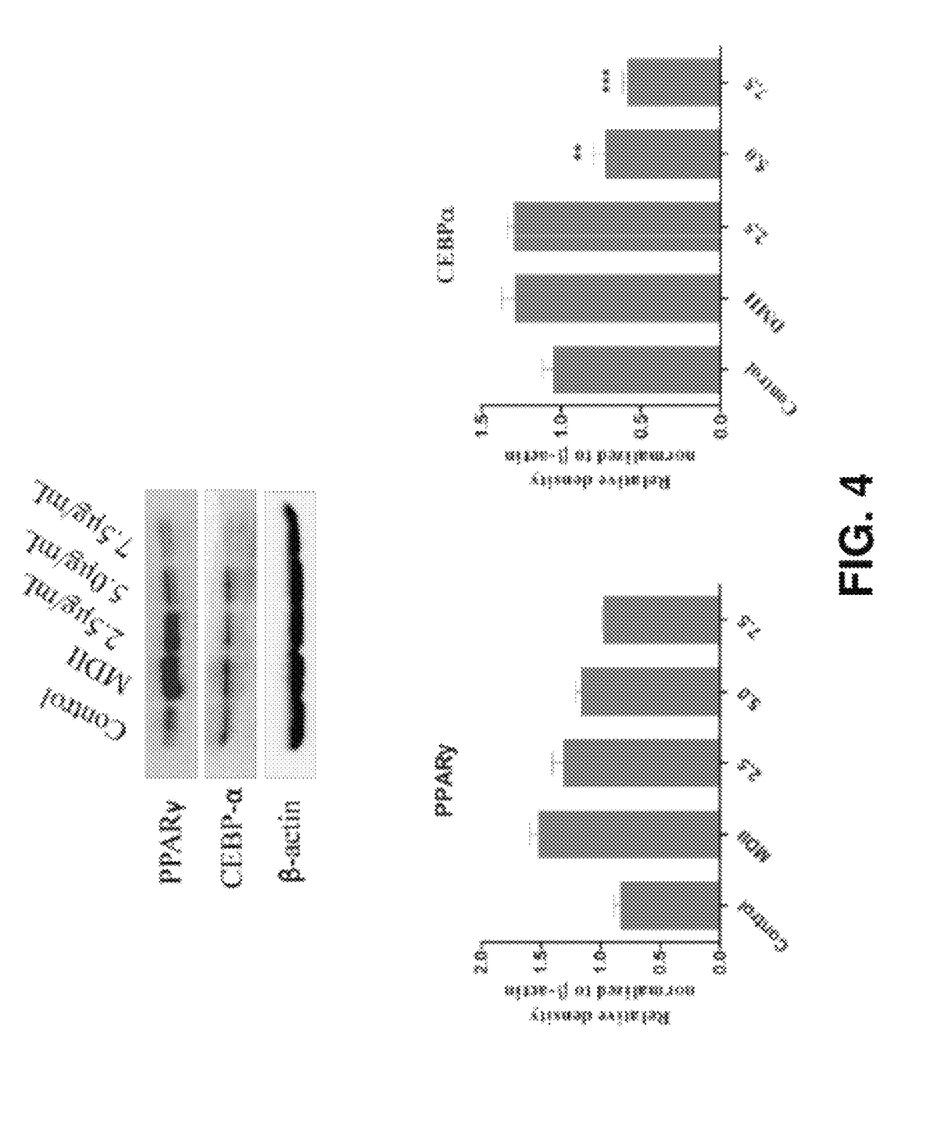
FIG. 4 shows a Western blot and graphs depicting the effects of the composition on PPARγ and C/EBPα protein expression.

FIG. 4 shows the effect of the composition on the expression of adipogenesis-related genes in 3T3-L1 adipocytes. Adipocytes were treated with various concentrations of the composition and were subjected to Western blotting using PPARγ and C/EBPα antibodies. Data are presented as means±SE. ** p<0.01 compared to the control. Expression levels of PPARγ and C/EBPα protein were dose dependently decreased in MDI+composition samples compared to MDI alone (FIG. 4). At a concentration of 7.5, μg/ml, the composition significantly down-regulated protein expression levels (p<0.01).

Regulation of Akt and PI3K During Adipocyte Differentiation

To determine whether the composition changed the phosphorylation levels of molecules that were downstream of insulin signaling, 3T3-L1 adipocytes were treated with DMII alone or with DMII and CAF. Lysates were collected and immunoblotted with phospho-Akt (Ser473), and phospho-PI3k antibodies. In the MDI and MDI+composition samples, MDI stimulation of 3T3-L1 adipocytes resulted in a significant increase in the phospho-Akt and phospho-PI3K proteins.

Figure 5:
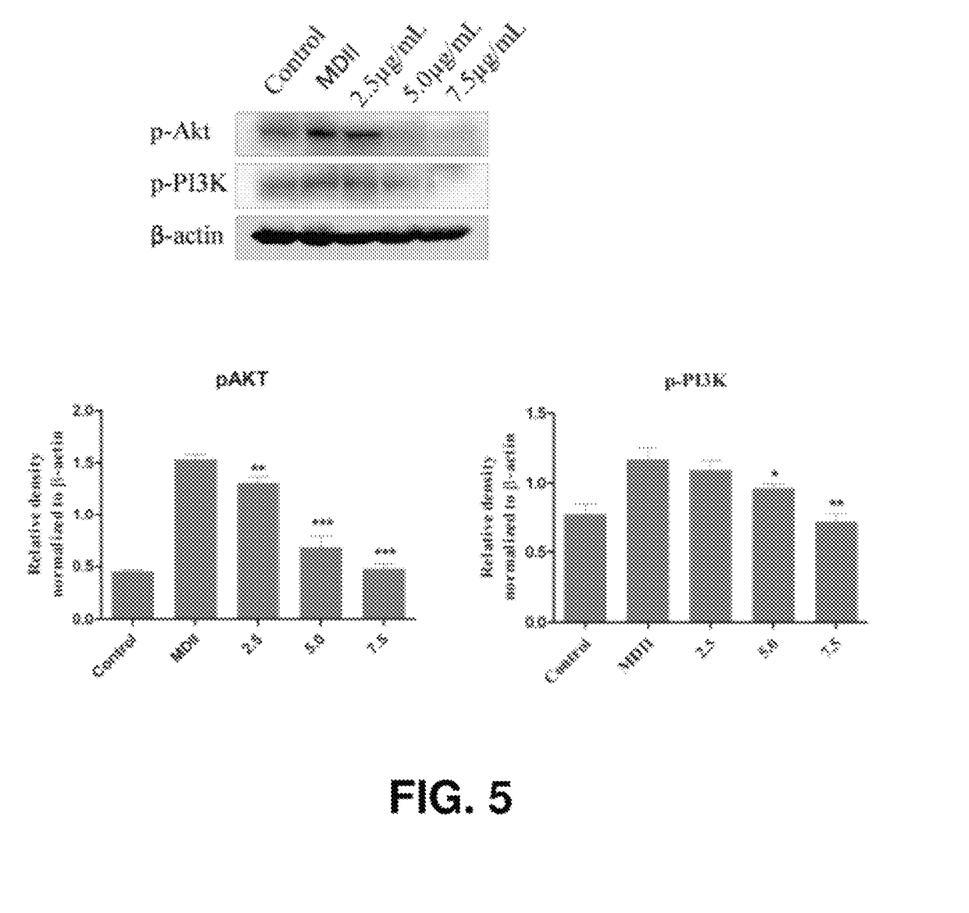
FIG. 5 shows a Western blot and graphs depicting the effects of the composition on phospho-Akt and phospho-PI3K protein expression.

In the presence of the composition, the expression of phospho-Akt dramatically decreased in 3T3-L1 adipocytes (FIG. 5). Similar to phospho-Akt, the expression of phospho-PI3K during 3T3-L1 differentiation was also dramatically decreased by the composition. These results demonstrate that the composition inhibits the phosphorylation of Akt, which suppresses the phosphorylation of its substrate kinase PI3K. which acts upstream of PPARγ and C/EBPα in adipogenesis.

FIG. 5 shows the effect of the composition on phosophorylation of Akt and GSK3b during 3T3-L1 differentiation. 3T3-L1 preadipocytes were differentiated in the absence or in the presence of the composition for 6 days. The experiments were performed as independent experiments in triplicate. Data represent the mean±SD. (*) $p<0.05$.

CONCLUSION

In conclusion, the composition inhibits pancreatic lipase activity, inhibits lipid accumulation in 3T3-L1 adipocytes, and inhibits the expression of adipogenesis-related proteins without cell cytotoxicity.

REFERENCES

1. Kim Y. S., Lee Y. M., Kim H., Kim J., Jang D. K., Kim J. H., Kim J. S. Anti-obesity effect of *Morus bombycis* root extract: Anti-lipase activity and lipolytic effect. J. Ethnopharmacol. 2010; 130:621-624.
2. Zheng C. D., Duan Y. Q., Gao J. M., Ruan Z. G. Screening of anti-lipase properties of 37 traditional Chinese medicinal herbs. J. Chin. Med. Assoc. 2010; 73:319-324.

The invention claimed is:

1. A method for promoting a healthy body weight, comprising administering to a patient in need thereof an effective amount of a composition comprising rosemary extract wherein said rosemary extract comprises about 50% w/w ursolic acid and said rosemary extract inhibits pancreatic lipase activity by about 50% at a concentration of about 20.68μg/ml in vitro.

2. The method of claim 1, wherein administering said composition reduces body weight in said patient.

3. The method of claim 1, wherein administering said composition prevents or inhibits weight gain in said patient.

4. The method of claim 1, wherein administering said composition maintains said patient's body weight.

5. The method of claim 1, wherein administering said composition reduces body fat in said patient.

6. The method of claim 1, wherein administering said composition prevents or inhibits fat gain in said subject.

7. The method of claim 1, wherein said patient is overweight.

8. The method of claim 1, wherein said patient is obese.

9. The method of claim 1, wherein said composition is administered at a dose of about 50 mg per kilogram of bodyweight, about 100 mg per kilogram of bodyweight, about 150 mg per kilogram of bodyweight, or combinations thereof.

10. The method of claim 1, wherein said composition is administered one or more times.

11. The method of claim 1, wherein said composition is administered daily, weekly, monthly, or combinations thereof.

12. The method of claim 1, wherein said composition is administered in a form selected from the group consisting of a powder, liquid, pill, tablet, pellet, granule, capsule, soluble film, solution, spray, syrup, linctus, lozenge, pastille, chewing gum, chew, paste, vapor, suspension, emulsion, ointment, cream, lotion, foam, liniment, drop, topical patch, buccal patch, bead, gummy, gel, sol, injection, and combinations thereof.

13. The method of claim 1, wherein said composition further comprises at least one of a vitamin, mineral, amino acid, protein, carbohydrate, lipid, fatty acid, excipient, pharmaceutical carrier, bulking agent, binding agent, caffeine, flavoring, sweetener, and preservative.

14. The method of claim 1, wherein said composition is combined with a food, snack, nutritional supplement, dietary supplement, food supplement, beverage, or combinations thereof.

15. The method of claim 1, wherein said composition is administered systemically.

16. The method of claim 1, wherein said composition is administered by a route selected from the group consisting of orally, buccally, sub-lingually, and combinations thereof.

17. The method of claim 1, wherein said composition is administered orally.

18. The method of claim 1, wherein said patient is a human.

* * * * *